United States Patent [19]

Heden et al.

[11] Patent Number: 5,640,966

[45] Date of Patent: Jun. 24, 1997

[54] MEDICAL APPARATUS FOR ANALYZING ELECTRICAL SIGNALS FROM A PATIENT

[75] Inventors: Bo Heden, Dalby; Mattias Ohlsson; Lars Edenbrandt, both of Lund; Ralf Rittner, Hjaerup; Olle Pahlm; Carsten Peterson, both of Lund, all of Sweden

[73] Assignee: Siemens Elema AB, Solna, Sweden

[21] Appl. No.: 554,359

[22] Filed: Nov. 6, 1995

[30] Foreign Application Priority Data

Nov. 16, 1994 [SE] Sweden ................................ 9403950

[51] Int. Cl.$^6$ ................................................ A61B 5/0402
[52] U.S. Cl. .................................... 128/696; 128/731
[58] Field of Search ............................ 128/696, 731, 128/732, 734

[56] References Cited

U.S. PATENT DOCUMENTS 5,251,626 10/1993 Nickolls et al. .
5,280,792 1/1994 Leong et al. .

OTHER PUBLICATIONS

"Comprehensive Electrocardiology, Theory and Practice in Health and Disease," vol. 3, 1989, pp. 1527–1530.
"Physician's Guide to Marquette Electronics Resting ECG Analysis," 1988, p. 53.
"Artificiella neuronnätverk," Peterson et al., Kosmos, 1982, pp. 87–102.
"Neural Networks for Classification of ECG ST–T Segments," Edenbrandt et al., J. of Electrocardiology, vol. 5, No. 3, 1992, pp. 167–173.
"Artificial Neural Networks for the Electrocardiographic Diagnosis of Healed Myocardial Infarction," Hedén et al, Am. J. of Cardiology, vol. 74, Jul., 1994, pp. 5–8.

*Primary Examiner*—William E. Kamm
*Assistant Examiner*—Scott M. Getzow
*Attorney, Agent, or Firm*—Hill, Steadman & Simpson

[57] ABSTRACT

An analysis apparatus such as an ECG apparatus has a control unit which includes an artificial neural network for discovering signal-recording electrodes which are erroneously attached to a patient. At least one artificial neural network is taught by being fed measurement signals from both correctly recorded measurements and from erroneously recorded measurements. The artificial neural network is then able to identify erroneous attachments with great accuracy from recorded measurement signals.

21 Claims, 3 Drawing Sheets

8A-8F        10A-10F        12A-12F

MEDICAL APPARATUS FOR ANALYZING ELECTRICAL SIGNALS FROM A PATIENT

BACKGROUND OF THE INVENTION

1. Field of the Invention

The present invention relates to a medical analysis apparatus of the type having a predetermined number of electrodes for placement at specific locations on a patient in order to pick up electrical signals from the patient, and a control unit for determining, on the basis of a predetermined number of input signals generated from the recorded electrical signals, whether any of the electrodes is incorrectly attached to the patient.

2. Description of the Prior Art

As used herein, an "incorrectly attached" electrode means an electrode which has been placed in the wrong location and/or is not in good electrical contact with the patient. "Patient" refers to any living creature, but henceforth only human patients will be exemplified.

One such analysis apparatus of the above type is the Mingograf Model 740, Siemens-Elema AB, Sweden. This known analysis apparatus is an ECG analysis apparatus and utilizes ten electrodes which are applied to the patient at specific locations. One electrode is applied to each arm and leg and the six remaining electrodes are applied to the chest. The three electrodes applied to the left arm, right arm and left leg, respectively, can be used for bipolar sensing of the heart's electrical signals. The following combinations are then possible: sensing between the right and left arm electrodes (designated lead I), sensing between the right arm and left leg electrodes (designated lead II) and between the left arm and left leg electrodes (designated lead III). These three electrodes can also be combined in pairs via resistors to form an indifferent electrode for the third electrode. Accordingly, the electrodes for the left arm and left leg can be combined to form an indifferent electrode for the electrode on the right arm (designated lead aVR), the electrodes for the right arm and left leg can be combined to form an indifferent electrode for the electrode on the left arm (designated lead aVL) and the electrodes for the right arm and the left arm can be combined to form an indifferent electrode for the electrode on the left leg (designated aVF). These three extremity electrodes can therefore be utilized for sensing in up to six measurement channels (leads I, II, III, aVR, aVL and aVF).

The six chest electrodes are designated V1–V6 and are applied to the chest in a specific sequence. The electrode on the right leg is grounded.

The ECG analysis apparatus further includes a control unit for determining whether the electrodes for the right and left arms have been correctly applied to the patient, i.e., whether the electrode for the right arm really has been placed on the right arm and whether the electrode for the left arm really has been placed on the left arm, and not the reverse. The control unit is programmed with a specific analysis program for performing this check. The analysis program uses certain signal parameters as input signals, derived from the measurement signals picked up by the electrodes. If the analysis program determines that an electrode placement mistake has occurred, an error message is generated which reports the suspicion of erroneous electrode application.

Discovering erroneously applied electrodes is important, since proceeding to obtain measurement signals with incorrectly placed electrodes could cause a wrong diagnosis to be made. This applies to, e.g., modern ECG analysis apparatuses equipped with different analysis programs for evaluating recorded measurement signals. The measurement signals must be recorded in the correct manner for these programs to work properly.

Detecting erroneously applied electrodes, e.g. the above left-to-right reversal of electrodes, from the recorded ECG tracks can be difficult. In principle, this reversal means that measurement signals for leads II and III and for leads aVL and aVR are reversed and the signal on lead I is simultaneously inverted. The wide variation is signal appearance found in correctly recorded ECGs, however, means that not even highly experienced physicians can easily identify certain erroneously recorded ECGs.

Incorrectly attached electrodes might appear to be a problem which can be solved with careful routines for staff to be followed when applying the electrodes to the patient. It should be remembered, however, that an estimated 300 million ECG recordings are made each year world-wide. Even if the percentage of incorrectly attached electrodes is very small, a large number of ECG recordings could still be made with incorrectly attached electrodes. Further, incorrect attachment does not necessarily entail application of one or several electrodes to the wrong site. Correctly located electrodes whose electrical contact with skin is poor may also be involved. Poor electrical contact could result in the electrode's failure to record information important to the diagnosis. An incorrect diagnosis could lead to incorrect treatment, no treatment etc. Most state of the art computerized ECG analysis apparatuses thus incorporate some analysis program, as noted above, for identifying electrode reversal on the right and left arms.

The known analysis programs, however, are only able, in principle, to identify reversal of electrodes on the right and left arm. Other erroneous connections, such as reversal of the electrodes on the left arm and left leg, are much harder to detect, and no analysis program has been devised for detecting them.

One of these analysis programs, which is implemented in the above Mingograf Model 740, is known under the designation GRI and is described in "Comprehensive Electrocardiography, Theory and Practice in Health and Disease", Volume 3, Oxford, Pergamon Press Inc., 1989, page 1530.

Another of these analysis programs is described in the "Physician's Guide to Marquette Electronics Resting ECG Analysis", Dec. 88 000-90160-010, USA, page 53, and is implemented in equipment supplied by Marquette Electronics Inc.

Both of these analysis programs have relatively good specificity, i.e. they seldom supply an error indication when the electrodes have been correctly applied. These known analysis programs, however, have a sensitivity which is less reliable, i.e., they do not invariably supply an error indication when there is a genuine reversal of left and right arm electrodes. The sensitivity of these analysis systems is especially reduced when the ECG measurement signal lacks P waves. Examinations of a large number of ECG recordings has shown that sensitivity can drop to 30 to 40% for the two methods when the P wave is absent. In other words, the analysis methods only discover 30 to 40% of erroneous connection of electrodes on the right and left arms.

SUMMARY OF THE INVENTION

An object of the present invention is to provide an analysis apparatus of the above type which is capable of identifying erroneous connections on the right and left arms with greater sensitivity than known analysis systems without impaired specificity.

Another object of the invention is to provide such an analysis apparatus which is additionally capable of identifying other types of incorrectly applied electrodes.

These objects are achieved in an analysis apparatus constructed in accordance with the principles of the present invention which has a control unit including an artificial neural network for determining whether the electrodes have been correctly applied to the patient.

Artificial neural networks (ANN) are well-known in a number of different fields. In principle, an ANN simulates the biological brain's ability to recognize patterns (complex and non-linear patterns in particular) and to make associations based thereon. The first ANN models were created as early as the 1940's but did not achieve a breakthrough until non-linearity was incorporated into the models in the 1980's. A brief history and basic description of the ANN is provided in the article "Artificiella neuronnätverk" by C. Peterson and T. Rögnvaldsson, KOSMOS 1992, pp. 87–102, Swedish Association of Physicists.

In recent years, ANNs have even been used in ECG technology, primarily as an aid in, e.g., the diagnosis of various disorders. With the aid of a very large number of ECG recordings, different ANNs have been devised and taught to identify and diagnose various pathological conditions.

A large number of studies has been performed and articles written on the use of ANNs in diagnosis, e.g., "Neural Networks for Classification of ECG ST-T Segments", Edenbrandt et al., Journal of Electrocardiography, Volume 25 No. 3, Jul. 1992, and "Artificial Neural Networks for the Electrocardiographic Diagnosis of Healed Myocardial Infarction", Hedén et al., The American Journal of Cardiology, Volume 74, Jul. 1, 1994.

In the specific identification of incorrectly applied electrodes in ECG recordings in accordance with the invention, the analysis apparatus can be an ECG analysis apparatus designed for sensing electrical signals from the patient's heart activity. For other measurements, the analysis apparatus can be an EEG analysis apparatus, or some other analysis apparatus which measures electrical signals in a patient.

It is advantageous for the artificial neural network used in the inventive apparatus to consist of three layers, i.e., an input layer with preferably up to twenty-five input neurons, a hidden layer with preferably four to six hidden neurons and an output layer with preferably one output neuron, and to have been taught on the basis of previous, correctly and erroneously recorded ECG measurement signals with the aid of a back-propagation algorithm. The hidden neuron can be of a sigmoid or radial base type with which data non-linearities can be processed. In instances in which data only contain linear relationships, the neural network operates in the manner of an ordinary linear multivariate separator. Such an artificial neural network is exceptionally general in adapting data.

In the teaching of the artificial neural network, it is advantageous if the back-propagation algorithm includes an asymmetrical error function, devised so the artificial neural network during teaching is "punished" harder for designating correctly connected electrodes as erroneous than for designating erroneously connected electrodes as correct. In this way, high specificity can be maintained. Alternatively, the same effect can be achieved with skewed sampling during the teaching process.

In one study covering more than 11,000 recorded ECGs, an artificial neural network was taught in this manner to recognize correctly and incorrectly applied electrodes on the right and left arms. An ECG with reversed electrodes on the right and left arms could be simulated from a correctly recorded ECG when the signal channels for lead II and lead III and lead aVR and aVL were switched and the signal for lead I was inverted. The specificity of the taught ANN was as good as that displayed by the known analysis methods and its sensitivity was better. Even when the P wave was absent in the ECG signal, the described artificial neural network retained very high sensitivity, more than 90%, a considerable improvement compared to the 30 to 40% of the known analysis methods.

Such an artificial neural network can be advantageously devised to determine whether electrodes on the patient's right and left arm respectively have been reversed.

Alternately, the artificial neural network can be taught to determine whether the electrodes on the left arm and left leg have been reversed. As noted above, no analysis method has hitherto been able to detect this type of erroneous placement. It has sometimes been assumed, even by those highly knowledgeable in the art, that such detection is impossible. But studies performed with specially taught artificial neural networks according to the invention nonetheless have shown that identification of even this type of erroneous application is possible. Specificity was high in these studies, nearly 100%, whereas sensitivity was lower, about 50%.

In a corresponding manner, the artificial neural network in the control unit of the inventive apparatus can be taught to identify a number of other erroneous applications, e.g. reversal of the V1–V6 electrodes on the chest.

The artificial neural network can also be devised to check or ascertain whether electrical contact between the patient and electrode is adequate or to optimize placement so the strongest signal strength is obtained for the respective measurement signal. An ECG is sensitive to interference near the electrodes, muscle twitching in particular. A small shift in the position of the electrode can result in better signal pick-up. In principle, this is an optimization problem an artificial neural network can solve.

According to the invention, the analysis apparatus can include a control unit having an artificial neural network which is capable of identifying a number of erroneous applications. Such an artificial neural network, however, requires more output neurons to achieve unambiguous identification of an erroneous connection or erroneous connections. One conceivable combination could be simultaneous determination of the erroneous application of electrodes to the left and right arms and to the left arm and left foot.

Alternatively, the control unit can be devised to have at least one additional neural network, the "first" artificial neural network being taught to identify a first, specific, erroneous application of electrodes and the additional artificial neural network being taught to identify a second, specific, erroneous application of electrodes. The control unit would then have a number of specialized artificial neural networks. One artificial neural network could then be taught to check for erroneous application of the electrodes to the right and left arms, and the additional artificial neural network could be taught to check for erroneous application of the electrodes to the left arm and left leg. More specialized artificial neural networks could naturally be implemented in the control unit, according to the erroneous applications whose rapid and reliable identification is deemed most important.

DESCRIPTION OF THE PREFERRED EMBODIMENTS

Figure 1:
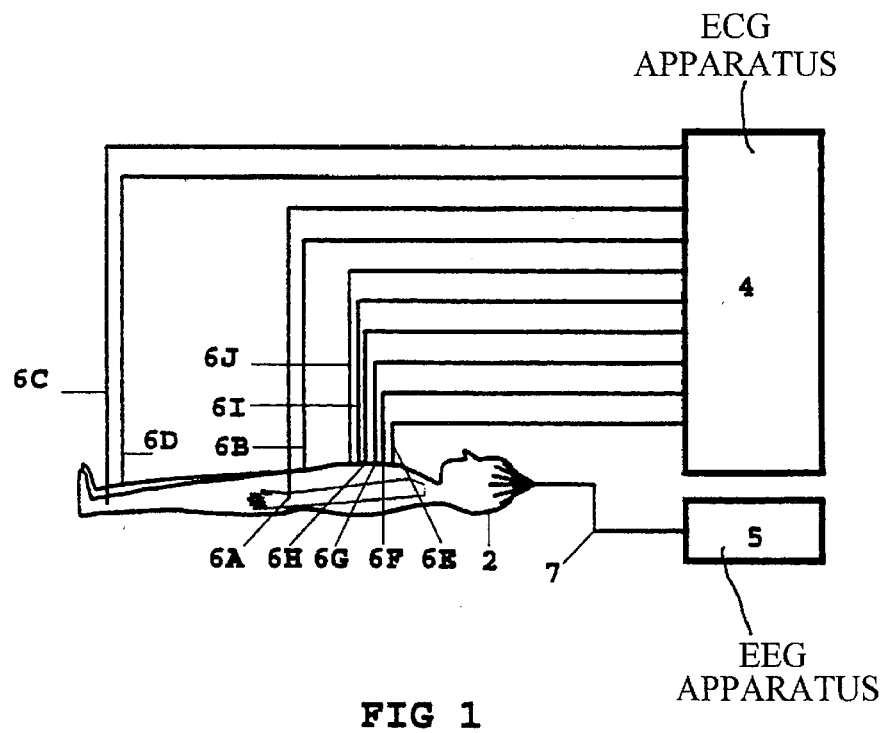
FIG. 1 schematically shows an ECG analysis apparatus constructed in accordance with the principles of the present invention connected to a patient.

FIG. 1 shows a patient 2 connected to an ECG analysis apparatus 4 via a plurality of electrodes 6A–6J. Here, the electrodes 6A–6J are placed at specific locations on the patient 2, i.e. a first electrode 6A is located on the left arm of the patient 2, a second electrode 6B is placed on the right arm of the patient 2, a third electrode 6C is placed on the left leg of the patient 2, a fourth electrode 6D is placed on the right leg of the patient 2 and the other electrodes 6E–6J are applied to the chest of the patient 2.

The first electrode 6A, the second electrode 6B and the third electrode 6C can be combined in different ways to create six lead combinations (=measurement channels), i.e. lead I, II, III, aVR, aVL and aVF. The way the electrodes 6A–6C are combined to achieve this is described above in conjunction with the description of the prior art.

It is extremely important for the electrodes 6A–6G to be correctly attached to the patient 2. A wrong diagnosis could be made if two or more measurement channels were mistakenly reversed because of erroneous placement of the electrodes 6A–6G. This is the case both when a physician evaluates resulting measurement signals and when the ECG apparatus 4 performs the evaluation.

Figure 2:
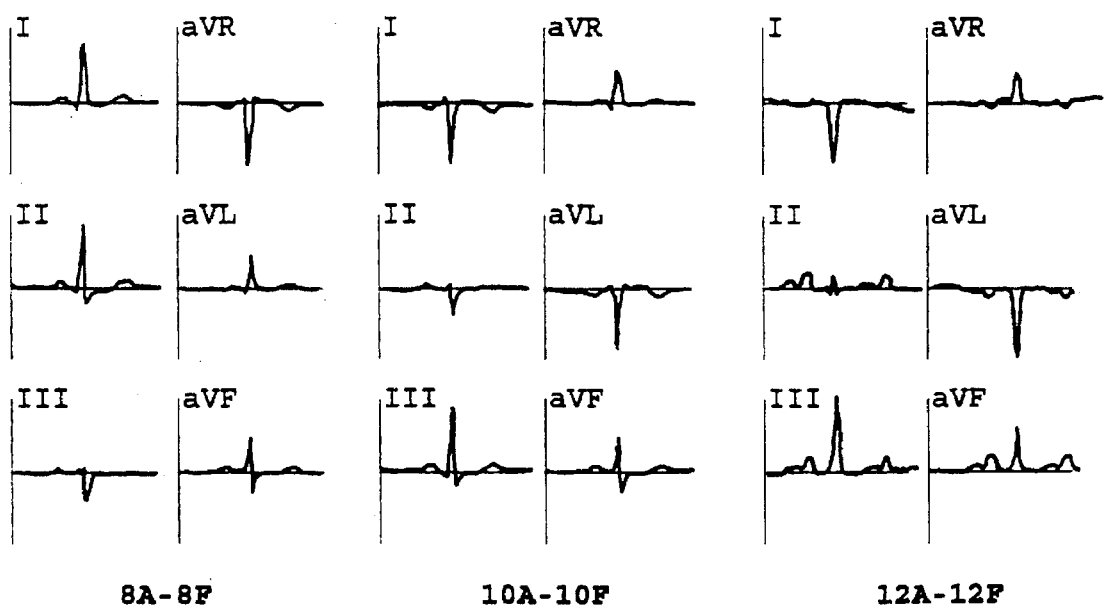
FIG. 2 shows ECG signals for correctly connected electrodes and for reversed electrodes on the right and left arms.

To the left in FIG. 2 are shown ECG measurement signals 8A–8F recorded from a patient with correctly applied electrodes. In the middle are shown ECG signals 10A–10F with simulated reversal of the electrodes on the right and left arms. To do this simulation, the channels II and III and aVR and aVL of the signals 8A–8F are reversed and channel I is inverted. To the right are shown ECG measurement signals 12A–12F recorded from another patient with correctly applied electrodes. This clearly shows that visual detection, from an individual ECG, of an erroneous application of two electrode:can be difficult, even when the electrodes for the right and left arms have been reversed. Thus electrode 6A on the left arm and electrode 6B on the right arm could be reversed without this being apparent in the resulting measurement signals.

A number of analysis methods have been devised (described above) for detecting this specific form of erroneous electrode application. They are normally included in modern ECG analysis apparatuses and issue a warning message when a reversal of the electrodes on the right and left arms is suspected. These analysis methods have relatively high specificity but poorer sensitivity. The sensitivity of these analysis methods is especially impaired when no P wave is present in the ECG signal.

Figure 3:
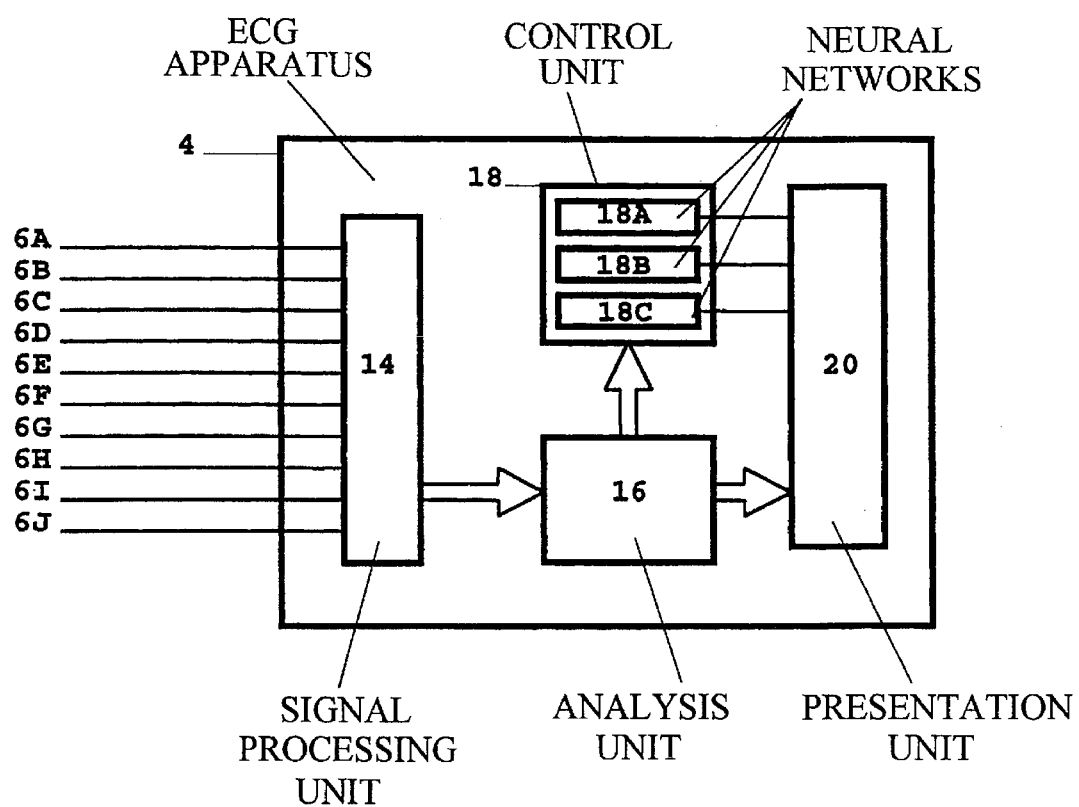
FIG. 3 is a block diagram of the ECG apparatus constructed in accordance with the principles of the present invention.

A new method for automatic detection of various erroneous electrode placements has therefore been developed in the present invention. FIG. 3 is a block diagram of an ECG analysis apparatus 4 designed for the new control method. The electrical signals generated by the heart are picked up by the respective electrodes 6A–6J and are fed to a signal processing unit 14 in the ECG analysis apparatus 4. The arriving signals are filtered, amplified and digitized in the signal processing unit 14 in the usual way for devices of this kind. The signal processing unit 14 also subdivides the signals into the six channels (I, II, III, aVR, aVL, aVF) created by the electrodes 6A, 6B and 6C.

The processed signals are sent via a databus to an analysis unit 16 which classifies the signals by differentiating among various signal parameters in the measurement signals. This differentiation can involve e.g. identification of the P wave, QRS complex and T wave as well as determination of amplitudes for same at different times. other signal parameters which can be differentiated are the duration and slope of PQRST waves and the interval between them.

A selection of these parameters is then sent via a databus to a control unit 18 for use as input signals for a first neural network 18A, a second neural network 18B and a third neural network 18C. The three neural networks 18A–18C are taught to identify different erroneous connections of the electrodes 6A–6J. Here, the first neural network can identify reversal of the first electrode 6A and the second electrode 6B, the second neural network 18B can identify reversal of the first electrode 6A and the third electrode 6C and the third neural network 18C can identify erroneous attachment of any of the electrodes 6E–6J to the chest.

If any of the artificial neural networks 18A–18C detects the presence of an erroneous attachment, it sends a signal to a presentation unit 20 to call the operator's attention to the suspected erroneous attachment.

The presentation unit 20 can contain e.g. an alarm unit which emits an acoustic alarm and a display which simultaneously indicates that an erroneous attachment/attachments is/are suspected.

The presentation unit 20 is also connected to the analysis unit 16 in order to display selected parts of the measurement signals and suggest diagnoses. Here, the analysis unit 16 contains all the required analysis and storage facilities normally found in modern, computerized ECG analysis apparatuses. One or a number of artificial neural networks can also be implemented in the analysis unit 16 in order to analyze and diagnose the measurement signals.

Figure 4:
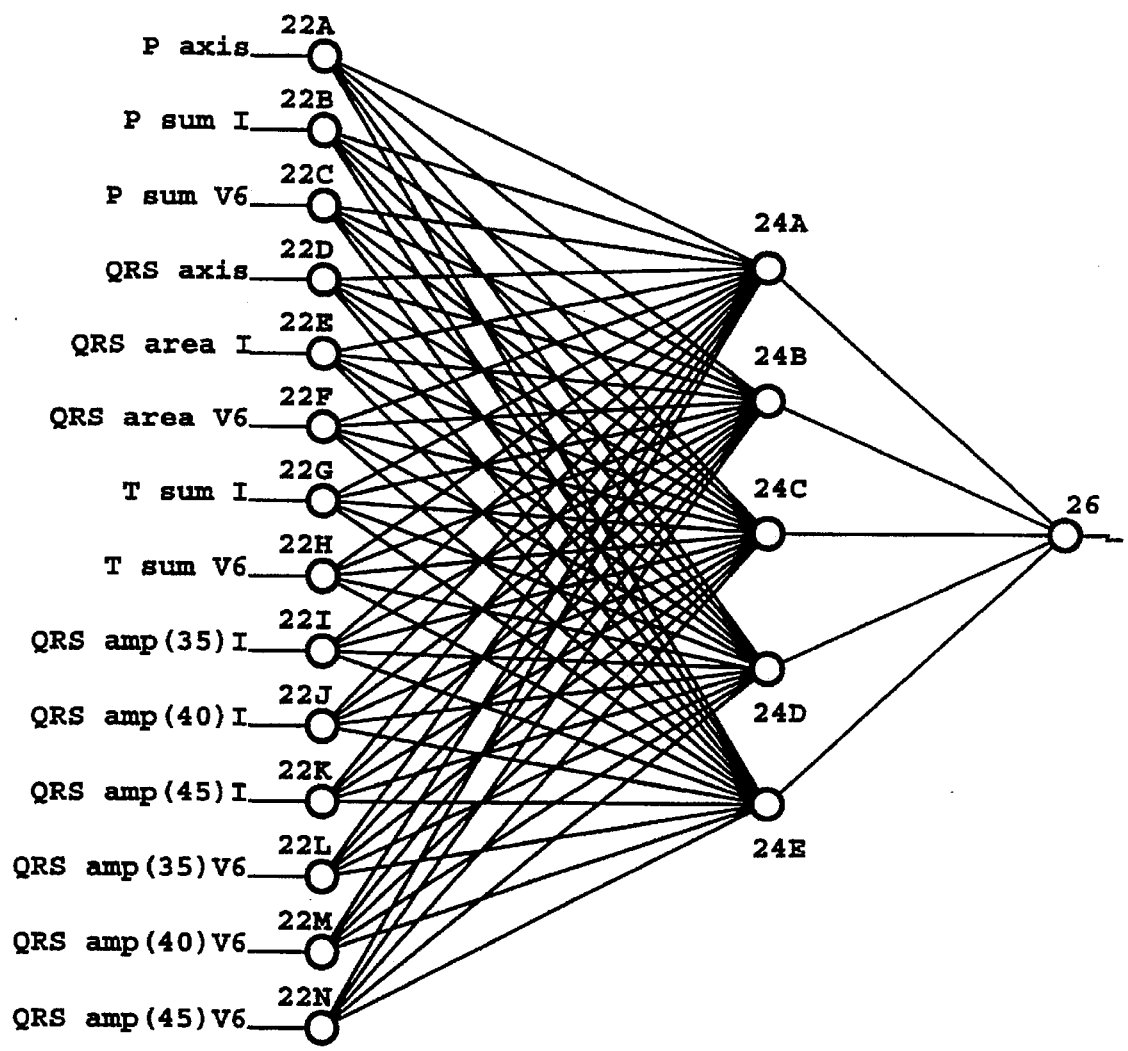
FIG. 4 shows a neural network for identifying electrodes reversed on the right and left arms employable in the apparatus of FIGS. 1 and 3.

One embodiment of the artificial network 18A for checking on the reversal of electrodes on the right and left arms is shown in FIG. 4. The artificial neural network 18A comprises three layers, i.e. an input layer with fourteen input neurons 22A–22N, a hidden layer with five neurons 24A–24E and an output layer with one output neuron 26. The artificial neural network 18A is devised so the output neuron 26 ideally emits a logic zero when the right and left electrodes are correctly connected and a logic one when these electrodes are reversed. Intermediate output signals with values less than 0.5 are interpreted as representing a correct connection, and output signals exceeding 0.5 are interpreted as representing an erroneous connection.

The signal parameters used as input signals for this artificial neural network 18A are indicated at input neurons 22A–22N. All input neurons 22A–22N are connected to each of the hidden neurons 24A–24E. All signals are summed, with different weights, in the usual way for artificial neural networks. Weights for the respective input signal and hidden neurons 24A–24E are determined during the teaching of the artificial neural network 18A with back-propagation. This teaching, however, is performed with an asymmetrical error function in order to achieve high specificity. Here, the artificial neural network is "punished" harder when it indicates that a correct connection is erroneous than when it indicates that an erroneous connection is correct.

The input signals, i.e. the signal parameters filtered out of the measurement signals, mainly from the measurement signal channels 1 and V6 in this instance, are largely identical to the input signals used as input signals by previously known error indication algorithms, such as Marquette's algorithm and GRI. Thus, these signal parameters, i.e. P axis, QRS axis, QRS area 1 and QRS area V6, are defined in descriptions of these analysis methods and therefore are familiar to anyone skilled in the art. The signal parameters new to analysis with the artificial neural network 18A are P sum 1, P sum V6, T sum 1, T sum V6, QRS amp(35)1, QRS amp(40)1, QRS amp(45)1, QRS amp(35)V6, QRS amp(40)V6, and QRS amp(45)V6. The term "sum" designates net amplitude, i.e. "P sum I" is the net amplitude of the P wave in channel I etc., and "amp(nn)" designates the amplitude at time nn ms after the start of the QRS complex. These signal parameters can easily be determined from the respective signal.

Devising the artificial neural network 18A with more or fewer input neurons and hidden neurons is possible. In principle, artificial neural networks can even be devised which use the same input signals as the Marquette algorithm and GRI. Trials with such neural networks have found improved neural network sensitivity.

In a corresponding manner, artificial neural networks can be devised to identify other erroneous placement of electrodes, e.g., reversal of electrodes on the left arm and left leg.

Devising a more comprehensive neural network capable of identifying different kinds of erroneous electrode placements is also possible. With, e.g., two output neurons, four ideal logic output signals can be obtained, 00, 01, 10 and 11.00 could then correspond to correct placement, 01 could correspond to reversed right and left electrodes, 10 could correspond to reversed left arm and left foot electrodes and 11 could correspond to both reversed right and left electrodes and reversed arm and foot electrodes. In the same manner described above, a logic zero could correspond to an output signal less than 0.5, and a logic one could correspond to an output signal greater than 0.5. An increased number of output neurons increases the ability to indicate more erroneous placements with an artificial neural network. In principle, one output neuron is required for each erroneous electrode placement to be identified for reliable, simultaneous indication of a number of erroneously placements.

Although the embodiment above mainly concentrates on the identification of erroneously applied electrodes, the invention is not limited to this application. Corresponding artificial neural networks can be devised for EEG analysis apparatuses to check the application of EEG electrodes. This has been indicated in FIG. 1., where an EEG analysis apparatus 5 is connected to the patient 2 via an EEG electrode system 7.

Artificial neural networks can, in particular, be taught to check whether there is good electrical contact between the patient's skin and the electrodes. In the embodiment above, the third neural network 18C, for example, can be devised to identify poor electrical contact.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus for analyzing electrical signals from a patient comprising:
   a plurality of electrodes respectively adapted for placement and attachment at defined locations on a patient to pick up electrical signals from the patient; and
   artificial neural network means, connected to each of said electrodes, for determining whether any of said electrodes is placed at a location on the patient differing from the defined location for that electrode.

2. A medical apparatus as claimed in claim 1 wherein said artificial neural network means additionally comprises means for determining whether any of said electrodes is incorrectly attached to said patient.

3. A medical apparatus as claimed in claim 1 wherein said plurality of electrodes comprise ECG electrodes for sensing electrical signals arising from cardiac activity of the patient, and said apparatus further comprising means for generating an electrocardiogram from said electrical signals.

4. A medical apparatus as claimed in claim 3 wherein said artificial neural network means comprises an input layer having a plurality of input neurons, a hidden layer having a plurality of hidden neurons, and an output layer having an output neuron, and wherein said input layer, said hidden layer and said output layer, in combination, comprise means teachable using a back-propagation algorithm with previously recorded correct and erroneous electrical signals obtained from said ECG electrodes.

5. A medical apparatus as claimed in claim 4 wherein said input layer comprises an input layer containing up to 25 input neurons.

6. A medical apparatus as claimed in claim 4 wherein said hidden layer comprises a hidden layer having said plurality of hidden neurons in a range of from 4 to 6 hidden neurons.

7. A medical apparatus as claimed in claim 4 wherein said output layer comprises an output layer having one output neuron.

8. A medical apparatus as claimed in claim 4 wherein said input layer, said hidden layer and said output layer comprise, in combination, means teachable with harder punishment for designating correctly placed ECG electrodes as incorrectly placed ECG electrodes than for designating incorrectly placed ECG electrodes as correctly placed ECG electrodes.

9. A medical apparatus as claimed in claim 4 wherein said plurality of ECG electrodes include a first ECG electrode adapted for placement on the right arm of the patient and a second ECG electrode adapted for placement on the left arm of the patient, and wherein said artificial neural network means comprises means for determining whether the respective locations of said first and second ECG electrodes on said patient are reversed.

10. A medical apparatus as claimed in claim 4 wherein said plurality of ECG electrodes include a first ECG electrode adapted for placement on the left leg of the patient and a second ECG electrode adapted for placement on the left arm of the patient, and wherein said artificial neural network means comprises means for determining whether the respective locations of said first and second ECG electrodes on said patient are reversed.

11. A medical apparatus as claimed in claim 1 wherein said artificial neural network means comprises means for identifying a first specific incorrect location of any of said electrodes, and said medical apparatus further comprising further artificial neural network means for identifying a second specific incorrect location of any of said electrodes, said first and second specific incorrect locations of said electrodes being different.

12. A medical apparatus as claimed in claim 1 wherein said plurality of electrodes comprise a plurality of EEG electrodes adapted to sense electrical signals arising from brain activity of the patient, and said medical apparatus further comprising means for producing an electroencephalogram from said electrical signals.

13. A method for analyzing electrical signals obtained from a patient comprising the steps of:

respectively placing a plurality of electrodes at defined locations on a patient; picking up electrical signals from the patient via said plurality of electrodes; and supplying said electrical signals from said electrodes to an artificial neural network; and analyzing said electrical signals in said artificial neural network and thereby determining whether any of said electrodes is placed on said patient at a location other than the defined location for that electrode.

14. A method as claimed in claim 13 comprising the additional step of:

analyzing said electrical signals in said artificial neural network to determine whether any of said electrodes is incorrectly attached to said patient.

15. A method as claimed in claim 13 wherein the step of respectively placing said plurality of electrodes at defined locations on a patient comprises respectively placing said plurality of electrodes at defined locations on a patient for sensing electrical signals arising from cardiac activity of said patient and thereby generating ECG measurement signals, and wherein said method includes the additional step of producing an electrocardiogram from said ECG measurement signals.

16. A method as claimed in claim 15 comprising the additional step of teaching said artificial neural network with a back-propagation algorithm using previously recorded correct and erroneous ECG measurement signals.

17. A method as claimed in claim 16 wherein the step of teaching said artificial neural network comprises teaching said artificial neural network with a back-propagation algorithm having an asymmetrical error function for punishing a designation of correctly connected electrodes as being incorrectly connected harder than a designation of incorrectly connected electrodes as being correctly connected.

18. A method as claimed in claim 15 wherein the step of respectively placing said electrodes at defined locations on a patient includes placing a first of said electrodes on a right arm of the patient and placing a second of said electrodes on a left arm of the patient, and wherein the step of analyzing said electrical signals in said artificial neural network includes identifying whether the respective locations of said first of said electrodes and said second of said electrodes are reversed.

19. A method as claimed in claim 15 wherein the step of respectively placing said electrodes at defined locations on a patient includes placing a first of said electrodes on a left leg of the patient and placing a second of said electrodes on a left arm of the patient, and wherein the step of analyzing said electrical signals in said artificial neural network includes identifying whether the respective locations of said first of said electrodes and said second of said electrodes are reversed.

20. A method as claimed in claim 13 wherein the step of analyzing said electrical signals in said artificial neural network comprises analyzing said electrical signals in said artificial neural network to identify whether a first specific incorrect location of said electrodes exists, and said method comprising the additional steps of supplying said electrical signals to a further artificial neural network, and identifying, in said further artificial neural network, whether a second specific incorrect location of said electrodes exists.

21. A method as claimed in claim 13 wherein the step of respectively placing said plurality of electrodes at defined locations on a patient comprises respectively placing said plurality of electrodes at defined locations on a patient to sense electrical signals arising from brain activity of said patient, and wherein said method comprises the additional step of producing an electroencephalogram from said electrical signals.

* * * * *